United States Patent
Quandt et al.

(10) Patent No.: US 8,758,636 B2
(45) Date of Patent: Jun. 24, 2014

(54) METHOD FOR PRODUCING A MEDICAL FUNCTIONAL ELEMENT COMPRISING A SELFSUPPORTING LATTICE STRUCTURE

(75) Inventors: Eckhard Quandt, Heikendorf (DE); Christiane Zamponi, Kiel (DE); Rodrigo Lima De Miranda, Kiel (DE)

(73) Assignee: ACANDIS GmbH & Co. KG, Pfinztal (DE)

( * ) Notice: Subject to any disclaimer, the term of this patent is extended or adjusted under 35 U.S.C. 154(b) by 126 days.

(21) Appl. No.: 13/322,998

(22) PCT Filed: May 28, 2010

(86) PCT No.: PCT/EP2010/003277
§ 371 (c)(1),
(2), (4) Date: Jan. 11, 2012

(87) PCT Pub. No.: WO2010/136215
PCT Pub. Date: Dec. 2, 2010

(65) Prior Publication Data
US 2012/0125888 A1    May 24, 2012

(30) Foreign Application Priority Data
May 29, 2009  (DE) .......................... 10 2009 023 371

(51) Int. Cl.
*C03C 15/00* (2006.01)
*B44C 1/22* (2006.01)
*H01L 21/027* (2006.01)
*H01L 21/768* (2006.01)
*H05K 3/04* (2006.01)

(52) U.S. Cl.
CPC ........ *H01L 21/0271* (2013.01); *H01L 21/7688* (2013.01); *H05K 3/048* (2013.01)
USPC ............................................. 216/36; 216/40

(58) Field of Classification Search
USPC ...................................................... 216/36, 40
See application file for complete search history.

(56) References Cited

U.S. PATENT DOCUMENTS

| 4,497,684 A * | 2/1985 | Sebesta .......................... 438/314 |
| 2002/0060297 A1* | 5/2002 | Konishi et al. ............. 250/492.1 |

(Continued)

FOREIGN PATENT DOCUMENTS

| DE | 102006029831 A1 | 1/2008 |
| WO | 0004204 A1 | 1/2000 |

(Continued)

OTHER PUBLICATIONS

International Search Report for PCT/EP2010/003277, English translation attached to original, Both Completed by the European Patent Office on Sep. 9, 2010, All together 8 Pages.

(Continued)

*Primary Examiner* — Shamim Ahmed
*Assistant Examiner* — Bradford Gates
(74) *Attorney, Agent, or Firm* — Brooks Kushman P.C.

(57) ABSTRACT

A method for producing a medical functional element having a self-supporting lattice structure which has interconnected webs. The method applies a first layer to the substrate layer, the first layer is structured by an etching process, the structured first layer is under-cut of a wet chemical etching process acting on the substrate layer, the substrate layer is removed in order to form the self-supporting lattice structure, a web constructional layer is applied to the first layer. The method is distinguished by the forming the first web attachment layer which has a smaller layer thickness than the web constructional layer and is intimately bonded to the web constructional layer in such a way that the web attachment layer, together with the web constructional layer, forms the webs of the self-supporting lattice structure.

17 Claims, 4 Drawing Sheets

(56) References Cited

U.S. PATENT DOCUMENTS

| | | |
|---|---|---|
| 2003/0024898 A1* | 2/2003 | Natsume et al. ............... 216/37 |
| 2004/0126707 A1* | 7/2004 | Liu et al. ....................... 430/320 |
| 2005/0244758 A1 | 11/2005 | Catchmark et al. |
| 2006/0284183 A1* | 12/2006 | Izumi et al. .................... 257/75 |
| 2007/0296395 A1* | 12/2007 | Uchida et al. ............. 324/76.55 |
| 2010/0009142 A1 | 1/2010 | Quandt et al. |

FOREIGN PATENT DOCUMENTS

| | | |
|---|---|---|
| WO | 0187371 A2 | 11/2001 |
| WO | 2007072247 A2 | 6/2007 |
| WO | 2008000467 A1 | 1/2008 |

OTHER PUBLICATIONS

Chun et al. "Micro patterning processes for thin film nitinol endografts and evaluation of endothelialization in swine model", Proc SPIE 2010, vol. 7650, 8 Pages.

* cited by examiner

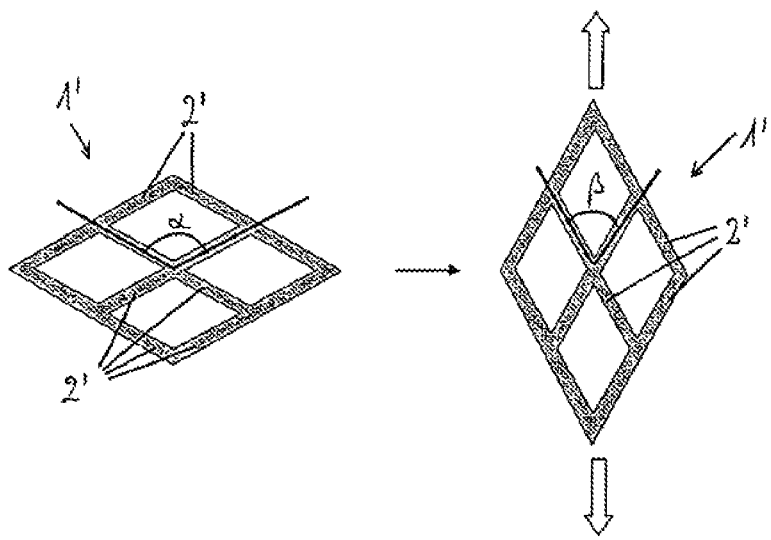
Fig. 2a
(Prior art)
Fig. 2b
(Prior art)
Fig. 3
(Prior art)

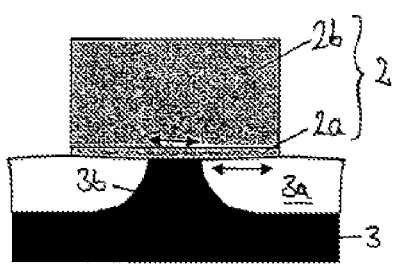
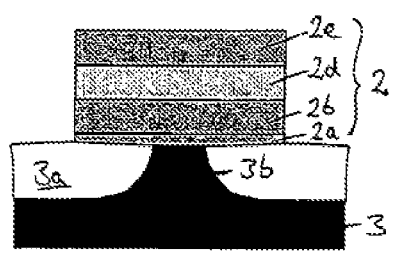
Fig. 7        Fig. 8
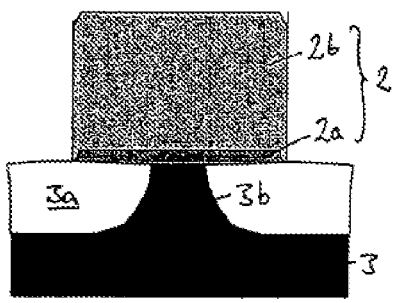
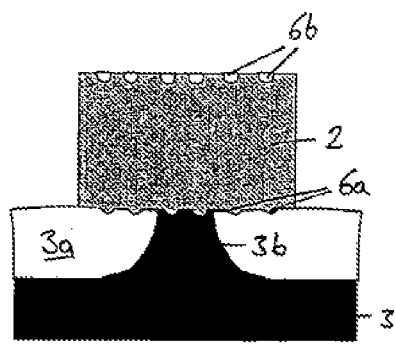
Fig. 9        Fig. 10

# METHOD FOR PRODUCING A MEDICAL FUNCTIONAL ELEMENT COMPRISING A SELFSUPPORTING LATTICE STRUCTURE

CROSS-REFERENCE TO RELATED APPLICATION

This application is the U.S. national phase of PCT Appln. No. PCT/EP2010/003277 filed May 28, 2010 which claims priority to German application 10 2009 023 371.7 filed May 29, 2009, the disclosures of which are incorporated in their entirety by reference herein.

TECHNICAL FIELD

The invention relates to a method for producing a medical functional element comprising a self-supporting lattice structure according to the preamble of claim 1. A method of this kind is known from WO 2008 000 467 A1, for example.

BACKGROUND

For the treatment of vascular lesions, particularly in cerebral vessels, with stents or generally tubular structures, it is expedient for the latter to have a high degree of flexibility. A high degree of flexibility improves the behavior of the stent in tightly curving vessels. When the stent curves, it lengthens, and the areas of the stent located on the outside of the vessel curvature expand or stretch more than the areas arranged closer to the center of the curvature. There is therefore a relationship between the flexibility, in the sense of being able to curve or bend, and the change in length or the maximum lengthening of the stent.

FIG. 1 is a schematic representation of the problem addressed by the invention. FIG. 1 shows a blood vessel comprising a first vessel portion 5a and a second vessel portion 5b, wherein a vessel curvature with a relatively small angle is formed between the first vessel portion 5a and the second vessel portion 5b. This means that the vessel curvature or vessel wall curvature between the second vessel portion 5b and the first vessel portion 5a is relatively tight. In order to place a stent in this area, it is therefore necessary that the stent is able to follow this vessel curvature. The required ability of the stent to curve or bend for this purpose is referred to in the context of the invention as flexibility.

Known stents comprise a lattice structure, which is produced from a tubular solid material by means of a method in which material is removed. As is shown in FIGS. 2a and 2b, the lattice structure 1' comprises a multiplicity of cells, which are defined by webs 2'. Here, the webs 2' are interconnected at an angle and form a rhomboid structure. In known stents, the degree of the change in length or the maximum lengthening is determined by changing the rhombus angle α, β. It is advantageous if the rhombus angle α in the rest state is relatively large (FIG. 2a) and the rhombus angle β in the stretched state is relatively small (FIG. 2b).

However, with a large angle difference between the rhombus angle α in the rest state and the rhombus angle β in the stretched state, there is a danger of the stent material undergoing plastic deformation at the connection points of the webs 2'. Moreover, a large rhombus angle α in the rest state of the stent means that considerable force has to be applied in order to bring the stent to the compressed state. This problem can be managed by reducing the volume of material at the connection points, for example by reducing the web width.

In stent production methods based on a laser cutting process, in which the lattice structure is formed from a tubular solid material by means of removal of material, the smallest possible dimensions of the web are limited on account of the thermal effects along the cutting edges.

In order to achieve smaller web dimensions, it is known to form the lattice structure of the stent by an etching method, with preference being given to the use of wet chemical etching processes, which permit a high speed of production. As is shown in FIG. 3, a web layer 2", which comprises the material of the lattice structure that is to be produced, is applied to a substrate layer 3'. The web layer 2" is applied in the layer thickness corresponding to the later web thickness. Moreover, a photoactive layer 4' is applied to the web layer 2" and, after suitable photo-lithographic treatment, forms an etching mask for the wet chemical etching process.

However, the wet chemical etching process also causes a lateral etching of the web layer 2' or an undercutting of the photoactive layer 4'. This means that the web layer 2" is also partially removed underneath the photoactive layer 4'. Consequently, the webs of the lattice structure that are produced by such methods have a trapezoidal profile, in which case relatively sharp edges form on the trapezoid base and can have a negative effect on the function of the stent. In particular, there is a danger of the sharp edges of the trapezoidal profile injuring the vessel walls or having a negative impact on the flow of blood in a blood vessel. Moreover, the webs produced by the wet chemical etching process according to the method known from the prior art have a relatively large web width, particularly on the trapezoid base, with the result that the flexibility of the known stent is further limited.

Therefore, in document WO 2008 000 467 A1 mentioned in the introduction, a method is proposed that permits the production of a lattice structure with increased edge precision of the webs. In this method, a sacrificial layer, which is structured using a photolithographic etching mask, is first of all applied to a substrate. The sacrificial layer is structured by a dry etching process in order to achieve the high degree of edge precision. In a further step, the substrate is subjected to a wet chemical etching process, as a result of which the sacrificial layer is undercut.

After removal of the etching mask, the stent material is then applied, in a sputtering process, to the laminate composed of substrate layer and sacrificial layer, with the stent material gathering in part on the sacrificial layer and in part on the etched substrate material. Following the removal of the substrate layer, of the sacrificial layer, and of the stent material embedded in the areas of the substrate layer etched by wet chemical etching, the desired self-supporting lattice structure remains.

A disadvantage of the method in WO 2008 000 467 A1 is that the sacrificial layer material, which preferably comprises gold, copper or chromium, is no longer available for the production process after removal or can only be reused by means of a complicated recycling process. Consequently, the known method is relatively expensive. Moreover, the removal of the sacrificial layer involves an additional method step, as a result of which more time is needed for the production of a stent.

SUMMARY

The object of the invention is therefore to improve the known method in terms of its profitability.

According to the invention, this object is achieved by the subject matter of claim 1.

The invention is based on the concept of making available a method for producing a medical functional element comprising a self-supporting lattice structure that has interconnected webs, in particular webs connected at an angle, which method comprises the following method steps:

A first layer applied to the substrate layer is made available.

The first layer is structured by an etching process.

The structured first layer is undercut by a wet chemical etching process acting on the substrate layer.

A web constructional layer is applied to the first layer.

The substrate layer is removed in order to form the self-supporting lattice structure.

The first layer forms a web attachment layer, which has a smaller layer thickness than the web constructional layer and is intimately bonded to the web constructional layer in such a way that the web attachment layer, together with the web constructional layer, forms the webs of the self-supporting lattice structure.

The principal aspect of the development is therefore to reduce the costs of the method by avoiding scrap material or sacrificial material. This is achieved by the fact that a web attachment layer is applied directly to the substrate layer and, together with the web constructional layer, forms the webs of the lattice structure that is to be produced. In this way, the web attachment layer contributes to the web thickness, as a result of which the production method is accelerated. Thus, through the use of the web attachment layer, the overall profitability of the method according to the invention is improved compared to conventional methods.

Since the first layer or web attachment layer contributes to the formation of the webs, the method according to the invention affords the further important advantage of improving the selectivity between the web attachment layer and the substrate layer. This means that the material of the web attachment layer or the etching agent can be chosen in such a way that, when the web attachment layer is undercut, damage to the web attachment layer is avoided. A particularly high degree of edge precision is achieved in this way.

The web attachment layer can have the same material as the web constructional layer, thus saving on processing time and material costs. The saving is achieved in particular by using a small number of different materials, in particular only two different materials, for example a first material for the substrate layer, and a common second material for the web attachment layer and web constructional layer that form the webs.

In a preferred embodiment of the method according to the invention, the web attachment layer is structured by a wet chemical etching process. Wet chemical etching has the advantage of faster processing compared to a dry etching method. It has been shown that, by applying a further material layer, in particular the web constructional layer, to the web attachment layer, the influence of the lateral etching on the edge precision is negligible. In particular, a high degree of edge precision is achieved with a relatively small layer thickness of the web attachment layer.

A further advantage of the wet chemical etching process is that the production costs and production time are reduced, since it is possible to dispense with additional facilities, for example installations for the dry etching, and with the processing steps carried out therein.

By means of the wet chemical etching process acting on the substrate layer, a catch basin is preferably made available in which scrap material is arranged upon application of the web constructional layer. The lattice structure that is to be produced is thus structured in a simple manner. In particular, the catch basin permits simple production of the cells of the lattice structure.

The catch basin can have an etching depth that is smaller than the layer thickness of the scrap material and/or of the web constructional layer. The production method is further accelerated by the relatively small etching depth. Furthermore, a small etching depth permits the production of a lattice structure with a small web width, since there is a geometrical relationship between the etching depth and the extent of the lateral etching and undercutting.

Since the catch basin has a smaller etching depth than the web constructional layer, the lateral etching of the substrate layer or the undercutting of the web attachment layer is additionally limited, such that the substrate layer underneath the web attachment layer forms a sufficiently wide support rib, which supports the web attachment layer.

A particularly preferred ratio between etching depth and layer thickness of the web constructional layer is one of less than 1:1, in particular less than 1:2, in particular less than 1:4, in particular less than 1:10.

In a preferred embodiment of the method according to the invention, the web attachment layer and/or the web constructional layer is formed by a physical deposition process, in particular a sputtering process. Such processes are distinguished by a high level of processing accuracy and a high processing speed.

At least one further web-forming layer can be applied to the web constructional layer. The method according to the invention is therefore suitable for the production of lattice structures whose webs have a laminate configuration. It is possible that the further web-forming layer has a material different from the web constructional layer, such that properties of different materials can be advantageously combined.

The further web-forming layer preferably comprises a bioabsorbable or X-ray-visible material, in particular tantalum. The method thus permits simple production of medical functional elements, in particular implants, which are distinguished by increased X-ray visibility. The biocompatibility of the implant can in this case be ensured by the X-ray-visible layer being embedded between two biocompatible layers.

In a preferred embodiment of the method according to the invention, the web attachment layer and the web constructional layer comprise a nickel-titanium alloy. A nickel-titanium alloy or generally a shape-memory material is suitable in particular for the production of medical functional elements that have self-expansion properties. In addition, nickel-titanium alloys are biocompatible.

Prior to the etching, the web attachment layer can be provided with a photoactive layer, which is subjected to a lithographic process and forms an etching mask in the shape of the lattice structure that is to be produced. The structuring of the web attachment layer and the resulting production of the lattice structure are facilitated and accelerated in this way.

The invention is explained in more detail below on the basis of illustrative embodiments and with reference to the attached schematic drawings, in which:

BRIEF DESCRIPTION OF THE DRAWINGS

FIGS. 2a, 2b show a detail of a lattice structure of a stent according to the prior art;

FIG. 3 shows a partial cross section through the lattice structure of a stent during production in a method according to the prior art;

FIGS. 7 to 10 show in each case a cross section through a web of a stent during production in a method according to the invention, in a preferred illustrative embodiment.

DETAILED DESCRIPTION

Figure 1:
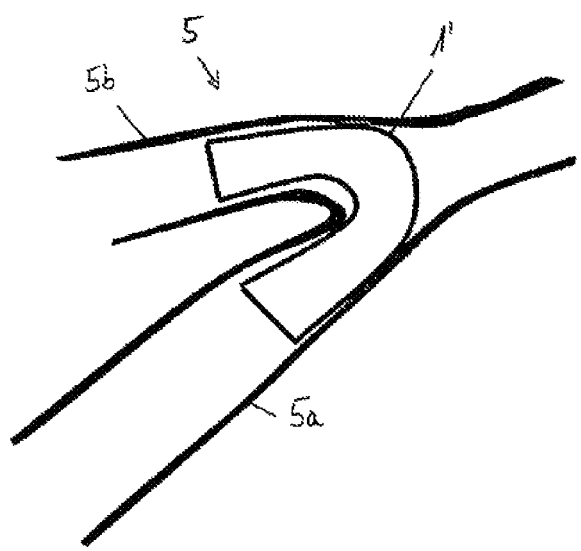
FIG. 1 shows a longitudinal section through a stent in the implanted state.
Figure 4:
FIGS. 4 to 6 show in each case a partial cross section through the lattice structure of a stent in a method step of the method according to the invention, in a preferred illustrative embodiment.
Figure 5:
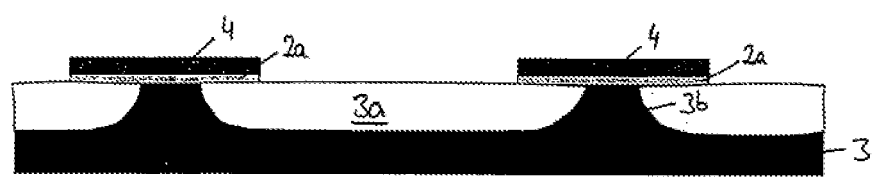
Figure 6:
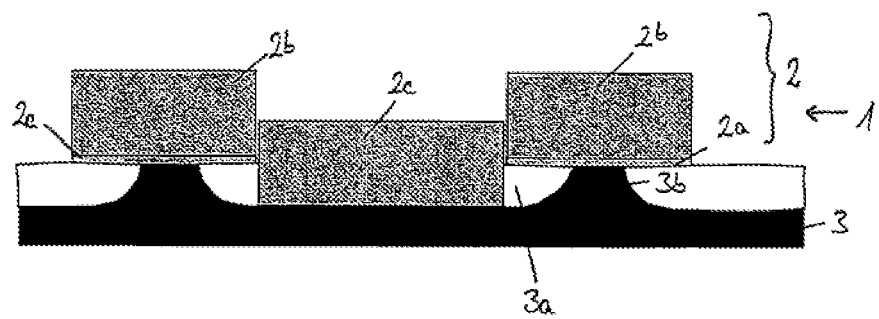

FIGS. 4 to 6 show selected method steps of the method according to the invention, in a preferred illustrative embodiment. The method is based on a web attachment layer 2*a* with a relatively small layer thickness being applied to a substrate layer 3, wherein the web attachment layer 2*a* has the material forming the webs 2 of the lattice structure 1 that are to be produced. The web attachment layer 2*a* is applied to the substrate layer 3 preferably by a physical deposition method, in particular by sputtering. The structuring of the web attachment layer 2*a* is effected through an etching mask, which is formed by a photoactive layer 4. The photoactive layer 4 or a photoresist layer is applied to the web attachment layer 2*a* and structured by a photolithographic process, for example by suitable exposure.

In a further method step (not shown), the web attachment layer 2*a* undergoes wet chemical etching, wherein the areas of the web attachment layer 2*a* located between the structured photoactive layer 4 are removed. The relatively small layer thickness of the web attachment layer 2*a* ensures that the degree of undercutting of the photoactive layer 4 by the wet chemical etching process is negligible. To this end, the web attachment layer 2*a* preferably has a layer thickness of between 0.025 μm and 5 μm, in particular between 0.05 μm and 4.5 μm, in particular between 0.1 μm and 4 μm, in particular between 0.25 μm and 3 μm, in particular between 0.5 μm and 2.5 μm, in particular between 0.8 μm and 1.5 μm. Furthermore, as is shown in FIG. 9, the laterally etched areas of the web attachment layer 2*a* are completed or filled, in a later method step, by the web constructional layer 2*b*, such that the lattice structure 1 produced has webs 2 with a high degree of edge precision.

After the structuring of the web attachment layer 2*a*, the substrate layer 3, in a further wet chemical etching process, is etched in the areas previously exposed using the etching mask. The web attachment layer 2*a* is thus undercut, as a result of which support ribs 3*b* of the substrate layer 3 form, which carry the web attachment layer 2*a* and the photoactive layer 4. Catch basins 3*a* are formed between the support ribs 3*b* by the etching process.

In order to obtain a sufficiently stable self-supporting lattice structure 1, it is necessary to increase the web thickness beyond the layer thickness of the web attachment layer 2*a*. For this purpose, in a further method step according to FIG. 6, a web constructional layer 2*b* is deposited on the web attachment layer 2*a* or the substrate layer 3 after the photoactive layer 4 has been removed. The web constructional layer 2*b* is preferably applied by a sputtering process. The web constructional layer 2*b* comprises the same material as the web attachment layer 2*a*. Preferably, the web attachment layer 2*a* and the web constructional layer 2*b* comprise a nickel-titanium alloy, which forms the webs 2 of the lattice structure that is to be produced. The layer thickness of the web constructional layer 2*b* is significantly greater than the layer thickness of the web attachment layer 2*a*. In particular, the web constructional layer 2*b* preferably has a layer thickness of at least 5 μm, in particular at least 8 μm, in particular at least 10 μm, in particular at least 12 μm, in particular at least 20 μm, in particular at least 30 μm, in particular at least 35 μm, in particular at least 40 μm, in particular at least 45 μm, in particular at least 50 μm.

During application of the web constructional layer 2*b*, some of the layer material is deposited as scrap material 2*c* in the catch basin 3*a* of the substrate layer 3. The scrap material 2*c* does not therefore contribute to the construction of the lattice structure.

The catch basin 3*a* preferably has a depth, or etching depth, that is smaller than the web thickness resulting from the sum of the layer thicknesses of the web constructional layer 2*b* and of the web attachment layer 2*a*. The ratio between the etching depth of the catch basin 3*a* and the layer thickness of the web constructional layer 2*b* can preferably be less than 1:1, in particular less than 1:2, in particular less than 1:4, in particular less than 1:10. For example, the etching depth measures 5 μm, in which case the layer thickness of the web constructional layer 2*b* measures 50 μm. It is particularly expedient if the ratio between etching depth and web thickness is adapted such that, when the web attachment layer 2*a* is undercut, a sufficiently wide support rib 3*b* is made available for supporting the web attachment layer 2*a*.

It is thus possible to reduce the undercutting or lateral etching of the catch basin 3*a*. For physical reasons, the ratio between the depthwise etching and the lateral etching is generally 1:1. With a web width of 15 μm and an etching depth of 5 μm, there is therefore a lateral etching of 5 μm. The substrate layer 3 forms a support rib 3*b* with a residual width of 5 μm, which supports the web attachment layer 2*a* during the subsequent application of the web constructional layer 2*b*.

If the etching depth is smaller than the layer thickness of the web constructional layer 2*b* or of the scrap material 2*c*, the scrap material 2*c*, together with the web constructional layer 2*b*, forms an overlap area (FIG. 6), which advantageously forms an additional, in particular lateral support for the web attachment layer 2*a*. Since the scrap material 2*c* gathers poorly on the perpendicular walls of the web constructional layer 2*b*, the scrap material 2*c* can be easily separated, in a subsequent method step, from the lattice structure or from the web 2, in particular from the web attachment layer 2*a* and the web constructional layer 2*b*.

The relationship between the width of the support rib 3*b* and the etching depth of the catch basin 3*a* is illustrated in FIG. 7. It can be seen from this that the wet chemical etching process has a substantially radial propagation. This means that material is removed from the substrate layer 3 to the same extent in all directions of propagation. The etching depth, or the depth of the catch basin 3*a*, thus corresponds to the depth of the lateral undercutting of the web attachment layer 2*a*. The aforementioned ratios are therefore particularly advantageous for ensuring that the web width of the lattice structure 1 that is to be produced is kept as small as possible and, at the same time, for providing a corresponding width of the support rib 3*b*, such that the web attachment layer 2*a* is sufficiently supported.

FIG. 8 shows another illustrative embodiment of the method according to the invention, wherein two further web constructional layers are applied to the web constructional layer 2*b*, which has a significantly greater layer thickness than the web attachment layer 2*a*. The web constructional layers can have different materials from the web constructional layer 2*b* and the web attachment layer 2*a*. The further web constructional layers can, for example, comprise an X-ray-visible layer 2*d*, which is arranged between the first web constructional layer 2*b* and a cover layer 2*e*. The X-ray-visible layer 2*d* preferably comprises tantalum or another X-ray-visible material, for example niobium, platinum, gold, or alloys with such materials. The cover layer 2*e* can have the same material as the web constructional layer 2*b* or the web attachment layer 2*a*. The layer thicknesses of the individual web constructional layers can vary. In particular, the X-rayvisible layer 2d can have a significantly smaller layer thickness than the web constructional layer 2b and the cover layer 2e.

It is also possible for the further web constructional layers to comprise partially bioabsorbable materials. For example, one or more further web constructional layers can comprise magnesium, iron, or alloys with magnesium and/or iron. The webs 2 can thus be composed of several web constructional layers 2b, or of a laminate comprising layers of X-ray-visible and/or bioabsorbable materials and/or shape-memory materials. The web attachment layer 2a can likewise comprise an X-ray-visible or bioabsorbable material. It is therefore possible that, for example, the web attachment layer 2a and/or the cover layer 2e each have a bioabsorbable material, such that the wall thickness of the webs 2 after implantation decreases over time. Stents produced by the method according to the invention thus have improved properties as regards the flow conditions in the blood vessel.

With the method according to the invention, it is possible, in another illustrative embodiment as shown in FIG. 10, to profile or structure the inner and outer surfaces of the webs 2. The uniform application of the web attachment layer 2a or web constructional layer 2b by the sputtering process, or generally by the physical deposition method, has the effect that structures incorporated into the substrate layer 3 are transferred to the surface of the web attachment layer 2a and then to the web constructional layer 2b. Wave profiles, projections 6a or cavities 6b are preferably incorporated into the substrate layer 3 and appear correspondingly in the surface of the web constructional layer 2b. The profiling or structuring of the substrate layer 3 can be done by an etching process, in particular a wet chemical etching process, or by another material-removing method, for example by a laser.

In the illustrative embodiment according to FIG. 10, the underside of the formed web 2, that is to say the underside of the web attachment layer 2a, has a profile with projections 6a, which profile is distinguished in particular by an improved endothelialization. This means that, when the produced lattice structure 1 is used as a stent, the flow conditions of the blood on this side of the webs 2, in particular the inner side of the lattice structure 1, are improved and thus favor the adherence of endothelial cells. The cavities 6b formed on the top side of the web 2, which correspond to the projections 6a on the underside of the web 2, can be used as medicament depots for example. Other kinds of profiling or structuring of the webs 2 are possible. For example, cavities 6b and projections 6a can be provided alternately on both sides of the webs 2.

The invention is suitable in general for the production of medical functional elements, in particular stents, clot retrievers, (blood) filters, and implants. An advantage of producing medical microsystems of this kind by the method according to the invention lies in the high degree of edge precision and small web widths. This advantage is also afforded, for example, in the production of electrodes or microelectrodes, which are in particular implantable.

LIST OF REFERENCE SIGNS 1, 1' lattice structure
2, 2' web
2" web layer
3, 3' substrate layer
4, 4' photoactive layer
2a web attachment layer
2b web constructional layer
2d X-ray-visible layer
2e cover layer
3a catch basin
3b support rib
3c scrap material
5 blood vessel
5a first vessel portion
5b second vessel portion
6a projection
6b cavity
α rhombus angle in the rest state
β rhombus angle in the stretched state

The invention claimed is:

1. A method for producing a medical functional element, the method comprising:
   applying a first layer to a substrate layer;
   etching the first layer to form a lattice structured first layer;
   undercutting the structured first layer using a wet chemical etching process acting on the substrate layer and forming a catch basin in the substrate layer;
   applying a web constructional layer having substantially perpendicular walls to the first layer; and
   removing the substrate layer in order to form a self-supporting lattice structure having interconnected webs;
   wherein during the step of applying the web constructional layer, scrap material is formed in the catch basin and forms an overlap area with the web constructional layer;
   wherein the first layer forms a web attachment layer, which has a smaller layer thickness than the web constructional layer and is intimately bonded to the web constructional layer in such a way that the web attachment layer, together with the web constructional layer, forms the webs of the self-supporting lattice structure.

2. The method as claimed in claim 1, wherein the web attachment layer has the same material as the web constructional layer.

3. The method as claimed in claim 1, wherein in the etching step the web attachment layer is structured by a wet chemical etching process.

4. The method as claimed in claim 1, wherein the scrap material is formed such that it contacts and provides lateral support to the web attachment layer.

5. The method as claimed in claim 4, wherein the catch basin has an etching depth that is smaller than the layer thickness of the scrap material and/or of the web constructional layer.

6. The method as claimed in claim 5, wherein the ratio between etching depth and the layer thickness of the web constructional layer is less than 1:1.

7. The method as claimed in claim 1, wherein the web attachment layer and/or the web constructional layer are formed by a physical deposition process.

8. The method as claimed in claim 1, further comprising applying at least one further web-forming layer to the web constructional layer.

9. The method as claimed in claim 8, wherein the further web-forming layer has a material different from the web constructional layer.

10. The method as claimed in claim 8, wherein the further web-forming layer comprises a bioabsorbable or X-ray-visible material.

11. The method as claimed in claim 1, wherein the web attachment layer and the web constructional layer comprise a nickel-titanium alloy.

12. The method as claimed in claim 1, further comprising prior to etching, coating the web attachment layer with a photoactive layer, and subjecting the photoactive layer to a lithographic process to form an etching mask in the shape of the lattice structure that is to be produced.

13. The method as claimed in claim 5, wherein the ratio between etching depth and the layer thickness of the web constructional layer is less than 1:2.

14. The method as claimed in claim 5, wherein the ratio between etching depth and the layer thickness of the web constructional layer is less than 1:4.

15. The method as claimed in claim 5, wherein the ratio between etching depth and the layer thickness of the web constructional layer is less than 1:10.

16. The method as claimed in claim 1, wherein the web attachment layer and/or the web constructional layer are formed by a sputtering process.

17. The method as claimed in claim 8, wherein the further web-forming layer comprises tantalum.

* * * * *